United States Patent [19]

Zemlan et al.

[11] Patent Number: 5,397,712
[45] Date of Patent: Mar. 14, 1995

[54] METHOD TO AID IN THE DIAGNOSIS OF ALZHEIMER'S DISEASE

[75] Inventors: Frank P. Zemlan; Gary E. Dean, both of Cincinnati, Ohio

[73] Assignee: University of Cincinnati, Cincinnati, Ohio

[21] Appl. No.: 920,830

[22] Filed: Jul. 28, 1992

[51] Int. Cl.$^6$ .................... G01N 33/53; G01N 33/543
[52] U.S. Cl. ..................................... 436/518; 435/7.1; 435/7.21; 436/530; 436/531; 436/811
[58] Field of Search .............. 436/518, 811, 548, 63, 436/530, 531; 435/7.9, 290.27, 7.1, 7.21; 530/839, 387.1, 388.1

[56] References Cited

FOREIGN PATENT DOCUMENTS 8903993  5/1989  WIPO .

OTHER PUBLICATIONS

Selkoe et al, *Alzheimer's and Parkinson's Diseases,* Fisher et al (Ed), 37–38 (1986).
Selkoe, D. J., Neurobiol. of Aging, 7:425–432 (1986).
*B. M. Biochemicals,* p. 68 (1991).
Mehta, et al, The Lancet, Jul. 6, 1985, p. 35.
Ihara et al, Nature, 304:727–730 (1983).
Vogelsang et al: Journal of Neurochemistry, vol. 54, No. 1, 1990, pp. 148–155.
Ghanbari et al.: Journal of the American Medical Publication, vol. 263, No. 21, pp. 2907–2910.

*Primary Examiner*—Carol E. Bidwell

[57] ABSTRACT

A method to aid in the diagnosis of Alzheimer's disease in a living patient is disclosed which tests cerebrospinal fluid (CSF) obtained from the patient. The CSF is tested using a Western blot analysis to determine the presence of an antigen present in soluble paired helical filaments which specifically binds to the monoclonal antibody produced by hybridoma ATCC HD11079.

2 Claims, 1 Drawing Sheet

METHOD TO AID IN THE DIAGNOSIS OF ALZHEIMER'S DISEASE

Government Rights

Research leading to the discovery of the current invention was funded in part by a government grant from the National Institutes of Health grant number NIMH-MH43520. The United States Government may have certain rights in this invention.

BACKGROUND

Alzheimer's disease is a 100% fatal neurodegenerative disease characterized by a chronically deteriorating course of cognitive, and later vegetative function. The definitive diagnosis of Alzheimer's disease is made by pathologic examination of postmortem brain tissue in conjunction with a clinical history of dementia. The diagnosis of definite Alzheimer's disease cannot be made in living patients as it requires examination of brain which cannot be performed in living individuals for ethical reasons. The diagnosis of definite Alzheimer's disease is based on the presence in brain tissue of extensive infestation by neuritic (senile) plaques and neurofibrillary tangles (NFT) whose density in brain are correlated with the severity of the clinical symptoms of the disease. The purpose of the present invention is to provide a laboratory based diagnostic test to allow the definite diagnosis of Alzheimer's disease in living patients by utilizing patient samples more accessible than brain.

Paired helical filaments are the only known pathological protein common to the two major neuropathological features which define Alzheimer's disease, neurofibrillary tangles and senile plaques. The biochemical characterization of paired helical filaments has been impeded because of technical difficulties in purifying and solubilizing this protein, a problem only recently solved. (Journal of Neurochemistry, Vol. 54, 148–155, 1990).

Postmortem detection of paired helical filaments (PHF) has been previously reported (Journal of the American Medical Association, Vol. 263, 2907–2910, 1990). This ELISA based test employing the antibody Alz50 may be used for the postmortem diagnosis of Alzheimer's disease. However, this test appears of no value for the diagnosis of Alzheimer's disease in living patients as it exclusively utilizes postmortem Alzheimer's brain samples.

Paired helical filaments purified and solubilized from Alzheimer's brain have been further characterized utilizing polyacrylamide gel electrophoresis (PAGE) which separates the PHF into: 1) a broad band of immunoreactivity ranging in molecular weight from approximately 20 to approximately 300 kilodaltons and 2) a specific 66 kilodalton protein referred to as PHF AD66 protein.

Others have attempted to clinically detect Alzheimer's disease in living patients. Such an attempt is disclosed in Wischik's European Patent Application WO89/03993. The specific protein detected using the Wischik method is believed to be a 9.5 kilodalton fragment of the 66 kilodalton protein obtained from PHF. This protein is different and physically separable from the material comprising the broad band of immunoreactivity, which serves as the basis for the present application. Wischik, in order to obtain his 9.5 kilodalton protein and corresponding antibody employed extensive and excessive digestion to solubilize his PHF. This apparently made the derived monoclonal antibody relatively unreactive. Thus, the test itself has never obtained clinical success.

SUMMARY OF THE INVENTION

The present invention is premised on the realization that a clinical test for the diagnosis of Alzheimer's can be provided by an immunoassay using cerebrospinal fluid as the test fluid.

More particularly, the present invention is premised on the realization that polyclonal or monoclonal antibodies which are reactive with a large portion of the broad band of immunoreactivity isolated from paired helical filaments in fact react with components in cerebrospinal fluid to accurately detect Alzheimer's disease without providing false positive readings. In particular, polyclonal antibodies derived from purified paired helical filaments are suitable for use in a Western blot analysis of cerebrospinal fluid to clinically detect Alzheimer's disease.

The present invention will be further appreciated in light of the following detailed description and drawings in which:

DETAILED DESCRIPTION

Figure 1:
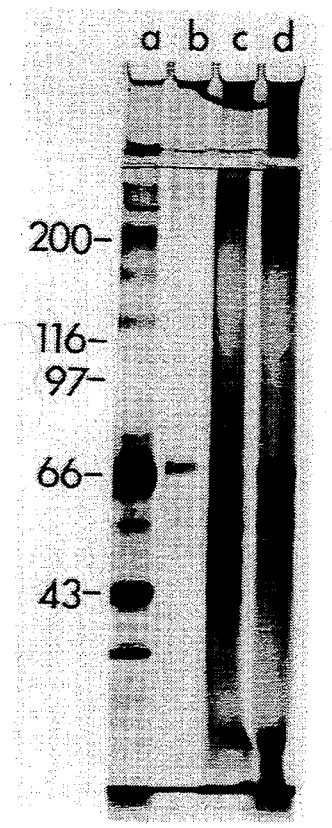
FIG. 1 is a silver stained SDS-PAGE analysis of paired helical filament fractions.

The present invention is an immunoassay (for example, Western blot, dot blot, or ELISA) for the detection of Alzheimer's disease which employs cerebrospinal fluid or blood plasma obtained from a patient as the test fluid. The antibody used in this test is a polyclonal or monoclonal antibody which is reactive with certain portions of the components forming paired helical filaments which are typically associated with Alzheimer's disease patients.

The polyclonal and monoclonal antibodies are raised against paired helical filaments and are defined based on their reactivity with certain components of these paired helical filaments. To establish this reactivity and thereby define the antibody, the paired helical filaments are purified and separated.

Paired helical filaments are obtained from brain tissue of deceased individuals with an autopsy confirmed diagnosis of Alzheimer's disease. The following is a procedure for the isolation and purification of paired helical filaments. Gray matter (5–6 g) from temporal or frontal cortex of histologically confirmed Alzheimer brain is dissected free of meninges, vessels, and white matter while immersed in cold phosphate-buffered saline (pH 9.8) containing 100 mM 2-mercaptoethanol.

More specifically, the cleaned gray matter is homogenized in a 55-ml Potter-Elvehjem tissue grinder driven by a constant torque motor drive (eberbach) in 0.32M sucrose with a loose-(clearance, 0.1–0.18 mm) and then a tight-(clearance, 0.1–0.15 mm) fitting pestle. The crude homogenate is sieved once through 105 micron nylon mesh and then three times through 75 micron mesh. The final volume of the crude material in 0.32M sucrose is 35 ml. The concentration of sucrose is increased to 1.0M, and then the mixture is layered over 25 ml of 1.2M sucrose in 50-ml polycarbonate test tubes and centrifuged at 800 g for 1 h using a TYH-4.2 rotor (Beckman). The pellets are reserved along with 2.0 ml of 1.2M sucrose from the bottom of each gradient, and the 1.0 and 1.2M sucrose layers are relayered over 25 ml of 1.2M sucrose and 6 ml of 1.8M sucrose, respectively. These gradients are centrifuged at 3,300 g for 45 min. The pellets of the 1.0–1.2M gradients and the interfaces of the 1.2–1.8M gradients are pooled with the pellets from the first 1.0–1.2M gradients.

To remove capillaries, this semicrude, neurofibrillary tangle-dense fraction is passed over a glass bead column consisting of glass beads 0.25–0.52 mm in diameter after diluting the homogenate to 0.32M sucrose. An equal volume of 0.32M sucrose is used to elute the NFTs from the column. The void volume and the eluate are centrifuged at 9,400 g for 1 h using a GSA rotor (Sorvall). Collagenase treatment of the pellets at 37° C., resuspended in 0.1M sodium phosphate (pH 7.4), 1 mM $CaCl_2$, and 20 ug of enzyme/mg of protein, is incorporated into the purification procedure at this point.

Pellets retrieved by centrifugation from the collagenase treatment or glass bead column alone are resuspended in 1.0% (wt/vol) SDS (1 ml/g of starting material) for 10 min at room temperature, and then the solubilized proteins are removed by centrifugation at 16,000 g for 30 min in an Eppendorf microfuge (Brinkmann model 5415). The pellets are resuspended in 0.1% (wt/vol) SDS (750 microliter) and layered in 150-microliter aliquots over an equal volume of 1.05M sucrose. The samples are centrifuged at 16,000 g for 30 min, and this last step is repeated two more times. The combined pellets contain relatively pure PHF [nontreated PHF ($PHF_N$)].

Next, 300–400 ug of $PHF_N$ (derived from 5–6 g of gray matter) is then placed in a chamber of a Schleicher and Schuell Elutrap device delimited by two highly selective membranes (BT1, $M_r$ cut off about 5,000), forming the most cathodal and anodal boundaries, and a third nonselective membrane (BT2) positioned between the two BT1 membranes. The device is submerged in a buffer containing Tris base (0.041M), boric acid (0.04M), SDS (0.8% wt/vol), and 5 mM 2-mercaptoethanol (pH 8.64), and a 100-V DC gradient is applied. The solubilized $PHF_s$ or copurified and associated proteins [soluble PHF ($PHF_a$)] migrate electrophoretically into the anodal chamber and can be removed at any time. Insoluble PHF ($PHF_I$) is retained on the cathodal side of the nonselective membrane.

For use in the ELISA or for SDS-polyacrylamide gel electrophoresis (SDS-PAGE), most of the $PHF_I$ and $PHF_S$ fractions are taken after 4.5 h of treatment, unless otherwise specified. The Tris/borate/SDS/2-mercaptoethanol buffer are removed and replaced by 0.32M sucrose in the $PHF_I$ fraction by pelleting at 16,000 g in a microfuge and resuspending the pooled pellets. $PHF_S$ samples are placed into a 10-ml disposable Novacell condensing stirrer (Pharmacia) equipped with a filter unit having an $M_r$ cutoff of about 5,000. The diluted sample is then alternately filtered under pressure and rediluted with at least 5 volumes of 0.1M $NH_4HCO_3$ (pH 8.12).

EXAMPLE 1

The three separate PHF samples $PHF_N$, $PHF_I$, and $PHF_S$ were isolated according to the above method and subjected to silver stained SDS PAGE analysis. All three revealed a strong band at about 66,000 and a broad continuous band ranging from 20 to 300 kilodaltons. This is shown in FIG. 1. In FIG. 1 Lane a contains molecular weight markers, Lane b $PHF_N$, Lane c $PHF_I$ and Lane d $PHF_S$. This broad band portion, most notable in Lanes c and d, is referred to as the broad band of immunoreactivity obtained from paired helical filaments. This was strongest at 60 to 300 kilodaltons.

The polyclonal and monoclonal antibodies that are useful in an immunoassay of Alzheimer's disease using cerebrospinal fluid are those polyclonal and monoclonal antibodies that are reactive to this broad band of immunoreactivity.

To obtain a polyclonal or monoclonal antibody which is suitable for this test, the $PHF_I$ and/or $PHF_S$ fragments can be injected into an appropriate mammal such as rabbits, mice, rats, etc. In one procedure, 200 micrograms of purified PHF pellet emulsified in Freund's adjuvant was injected subcutaneously into a rabbit. Four weeks later, rabbits received a booster of 200 micrograms of the PHF pellet in complete Freund's adjuvant. Sera taken from the rabbits will then strongly immunolabel NFTs derived from Alzheimer's disease cortex. The polyclonal antibody in this sera was separated to provide primary antibody solution. A more detailed description of this antibody's preparation and characterization are disclosed by Ihara et al. in Nature, Vol. 304, Aug. 25, 1983, page 727–730, entitled "Antibodies to Paired Helical Filaments in Alzheimer's Disease Do Not Recognize Normal Brain Proteins."

Hybridoma cells which produced monoclonal antibodies to $PHF_S$ were formed using standard techniques specifically injecting the protein into a mouse (Balb c female). Mouse spleen cells were fused with myeloma cells (P3X63-Ag8.653, Balb c origin nonimmunoglobulin producer). Cells which expressed the monoclonal antibody were selected by Western Blot and immunocytochemical analysis. Cells producing this monoclonal antibody to $PHF_S$ protein have been deposited with the American Type Culture Collection in Rockville, Maryland on Jun. 25, 1992 and have been given the ATCC number HB 11079. These cells can be employed to produce the antibody used to detect Alzheimer's disease by testing cerebral spinal fluid.

To test the effectiveness of the above polyclonal antibody solution, suspensions of $PHF_I$ and $PHF_N$ were formed by resuspending the pellets in a coating buffer (15 mM $Na_2CO_3$ and 35 mM $NaHCO_3$) to a concentration of 2 micrograms per milliliter as determined by amino acid analysis. The suspensions were then sonicated (4–20 sec. bursts at 45% maximal output) to create a solution. Several dilutions were made, resulting in five different concentrations with a five fold decrease in concentration between each sample.

Each concentration was plated in triplicate for these 2 PHF fractions. $PHF_S$ and crude Alzheimer's brain extracts from the initial homogenization during the PHF extraction were similarly plated. The 96-well microtitre plate, loaded with 100 microliters of either the antigen solution or coating buffer was allowed to incubate overnight at 4° C. The following day the plate was emptied and rinsed three times with washing buffer (310 mM NaCl, 17.5 mM $Na_2HPO_4$, 2.8 mM $NaH_2PO_4$ 0.9% $H_2O$ and 0.05% Tween 20, pH 9.8). After blocking for three hours at room temperature with 300 microliters of washing buffer containing 1.5% (wt/vol) bovine serum albumin and four rinses with washing buffer, 100 microliters of the primary antibody solution with 0.5%

(wt/vol) bovine serum albumin was pipeted into each well. After two hours of incubation, the plates were rinsed again and 100 microliters of the solution containing anti-rabbit IgG conjugated to alkaline phosphatase plus 0.5 (wt/vol) bovine serum albumin was placed into each well for two hours with gentle rotation. The washing procedure was repeated and then 100 microliters of the substrate four nitrophenylphosphate (1 mg per milliliter) and diethanol amine buffer pH 9.8 was allowed to react with the complexed enzyme for about one hour before the reaction was stopped with 50 microliters of three molar NaOH. The absorbances were determined by a Bio-Rad ELISA reader at a wavelength of 205 namometers. In these ELISAs, the described polyclonal and monoclonal antibodies demonstrated a concentration dependent immunoreactivity with both $PHF_I$ and $PHF_S$.

Antibodies suitable for use in this invention will react with the broad band of immunoreactivity purified from paired helical filaments as previously discussed. These antibodies do not react merely within the 66 kilodalton protein but along the entire band of 20 to 300 kilodaltons and particularly within the 60 to 300 kilodalton range.

The polyclonal antibody obtained according to the above *Nature* (1983, 304, 727–730) reference reacts with the broad band of immunoreactivity formed from paired helical filaments of Alzheimer's disease patients as previously discussed. This antibody failed to react with the 66 kilodalton AD66 protein component of PHF.

Thus, the polyclonal and monoclonal antibodies suitable for use in the present invention are those that react with the broad band of immunoreactivity as previously discussed. These antibodies are useful in performing a test on living patients to diagnose Alzheimer's disease. Specifically, cerebrospinal fluid is removed from the patient and tested using a Western blot analysis using the polyclonal or monoclonal antibodies previously identified to detect the presence of this broad band of immunoreactivity. Identification of this Alzheimer specific protein in the spinal fluid is a clear indication of Alzheimer's disease.

To accomplish this test, cerebrospinal fluid is loaded onto SDS-polyacrylamide slab gels made according to the procedure of Laemmli (*Nature*, 1970), 227:680–685). A 3% stacking gel is placed on top of the running gel. Gels are transferred to nitrocellulose using the method of Towbin et al (*Proc. Natl. Acad. Sci.*, 1979, 76:4350–4354). The transferring gel is equilibrated in transfer buffer (20% methanol, 192 mM glycine, 0.025M Tris base) for at least 30 minutes, as is the nitrocellulose paper. Transfer is effected over 8–12 hours at 5–10 V in a Hoefer Transphor unit. The following day the voltage is increased to 100 V for 1–2 hours or until current output reaches 1.2 amps. The transfers are removed from the Transphor unit and incubated in TBS (20 mM Tris, 150 mM NaCl) for 30 minutes.

All ensuing steps are done with slow continuous agitation. The transfers are blocked for 1 hour in 30 ml of Blotto (5% non-fat dry milk, TBS, 0.01% antifoam A [Sigma]). The transfers are washed three times in TBS and then incubated with the polyclonal or monoclonal antibody diluted in 3% BSA/TBS for 2 hours at room temperature. After washing the transfers three times with 0.5% BSA/TBS, transfers are reacted with second antibody, goat anti-rabbit IgG conjugated to $^{125}I$ (0.5 uCi/10 ml) diluted in 3% BSA/TBS for 1 hour at room temperature. Transfers are washed three times for 10 minutes each; once with TBS/0.5% BSA; once with TBS/0.5% BSA/0.1% Nonidet P-40; once with TBS. The immunostained transfers are left moist, wrapped in cellophane and autoradiographed at −80° C. for 1–3 days.

EXAMPLE 2

Figure 2:
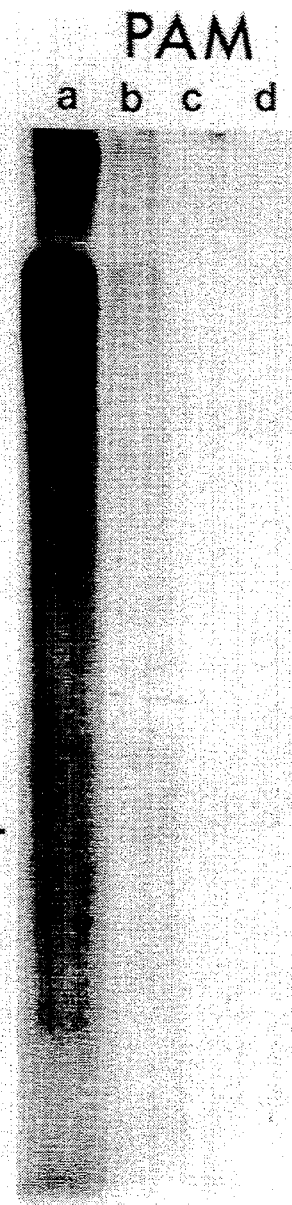
FIG. 2 is a silver stained SDS-PAGE analysis of paired helical filaments and cerebrospinal fluid obtained from patients with Alzheimer's disease, Parkinson's disease and Pick's disease.

This procedure was followed to produce FIG. 2 which is a transfer replica of a SDS-PAGE gel reacted with this antibody (1:500). Lane a represents 10 micrograms of purified PHF AD66 protein. Lane b represents 40 microliters of cerebrospinal fluid from an autopsy confirmed Alzheimer's patient. Lane c represents 40 microliters of cerebrospinal fluid from a Parkinson's patient. Lane d represents 40 microliter of cerebrospinal fluid from a Pick's patient.

The material in lanes a and b were both labeled with this antibody. Specifically, they were labeled throughout the 20 to 300 kilodalton range. The spinal fluid from the Parkinson's and Pick's patients were not labeled.

Thus, the present invention correctly identified cerebrospinal fluid from a patient with Alzheimer's disease. It does not provide false positive results for patients with Pick's or Parkinson's disease.

The present invention provides a very precise diagnostic test for detecting Alzheimer's disease in living patients. It is surprising that the antibodies useful in this test method are identifying not a precise protein, but a broad band of immunoreactivity isolated from material derived from Alzheimer's patent brains. Normal test methods would typically analyze for the presence of a very specific protein. However, the polyclonal and monoclonal antibodies identified do not react with a very precise protein isolated from paired helical filaments, but rather react with a broad band of Alzheimer's specific material possibly a glycolipid which does not resolve as a discrete band on SDS-PAGE. However, clinical test data have proven that this is an accurate detection method and that the described antibodies are not reactive with other proteins in cerebrospinal fluid. Thus, false positive readings are avoided.

The preceding has been a description of the method of practicing the present invention along with the preferred method currently known to the inventors. However, the invention should be defined only by the appended claims wherein.

We claim:

1. A method to aid in the diagnosis of Alzheimer's disease in a living patient comprising:
    combining cerebrospinal fluid (CSF) obtained from the patient with a monoclonal antibody which binds to an antigen present in soluble paired helical filaments, wherein the monoclonal antibody is produced by hybridoma having ATCC accession number HB11079 or binds to the same epitope as the monoclonal antibody produced by hybridoma having ATCC accession number HB11079; and
    detecting the specific binding reaction of the monoclonal antibody with the antigen present in the CSF, wherein the presence of the specific binding reaction indicates that the patient has Alzheimer's disease.

2. The method of claim 1 wherein the specific binding reaction of the monoclonal antibody with the antigen present in the CSF is detected using a Western Blot analysis.

* * * * *